United States Patent [19]

Palladino

[11] Patent Number: 5,082,658
[45] Date of Patent: Jan. 21, 1992

[54] GAMMA INTERFERON-INTERLEUKIN-2 SYNERGISM

[75] Inventor: Michael A. Palladino, San Mateo, Calif.

[73] Assignee: Genentech, Inc., San Francisco, Calif.

[21] Appl. No.: 488,486

[22] Filed: Mar. 2, 1990

Related U.S. Application Data

[63] Continuation of Ser. No. 904,824, Sep. 8, 1986, abandoned, which is a continuation of Ser. No. 571,174, Jan. 16, 1984, abandoned.

[51] Int. Cl.$^5$ ............... A61K 37/66; A61K 37/02; C07K 15/06; C07K 15/26
[52] U.S. Cl. ............... 424/85.2; 424/85.5; 530/351; 435/69.5; 435/69.52
[58] Field of Search ............... 424/85.2, 85.5; 530/351; 435/69.51, 69.52

[56] References Cited

U.S. PATENT DOCUMENTS 4,518,584  5/1985  Mark et al. ............... 435/68

FOREIGN PATENT DOCUMENTS 089062  9/1983  European Pat. Off. .

OTHER PUBLICATIONS

Lotze et al., J. Immunol., vol. 135, pp. 2865-2875, 1985.
Kasahara et al., J. Immunol., vol. 130, pp. 1784-1789, 1983.
Kawase et al, J. Immunol., vol. 131, pp. 288-292, 1983.
Weigent et al., Infection and Immunity, vol. 41, pp. 992-997, 1983.
Handa et al., J. Immunology, vol. 130, pp. 988-992, 1983.
Kuribayashi et al., J. Immunology, vol. 126, pp. 2321-2327, 1981.
Wakasugi et al., JNCI, vol. 69, pp. 807-812, 1982.
Dempsey et al, J. Immunology, vol. 129, pp. 2504-2509, 1982.
Chemical Abstracts, vol. 100, Abstract No. 49809t, 1984.
Chemical Abstracts, vol. 98, Abstract No. 213902f, 1983.
Teh et al., "J. of Immunology", 131(4):1827-1833 (Oct. 1983).
Watson et al., "Lymphokines" 6: Pick et al., ed. 95-115 (1982).
Hefeneider et al., "NK Cells and Other Natural Effector Cells", 421-426 (1982), Herberman ed.
Lattime et al., "J. Exp. Med.", 157:1070-1075 (Mar. 1983).
Henney et al., "Nature", 291:335-338, (28 May 1981).
Toribio et al., "Eur. J. Immunol.", 13:964-969 (1983).
Svedersky et al., "J. of Immunology", 133(2):714-718 (Aug. 1984).

*Primary Examiner*—Margaret Moskowitz
*Assistant Examiner*—R. Keith Baker
*Attorney, Agent, or Firm*—Ginger R. Dreger

[57] ABSTRACT

Compositions containing therapeutically synergistic mixtures of purified gamma interferon and purified interleukin-2 are provided for treatment of tumor-bearing hosts. Preferably, the gamma interferon and interleukin-2 are obtained from recombinant cell synthesis.

4 Claims, 1 Drawing Sheet

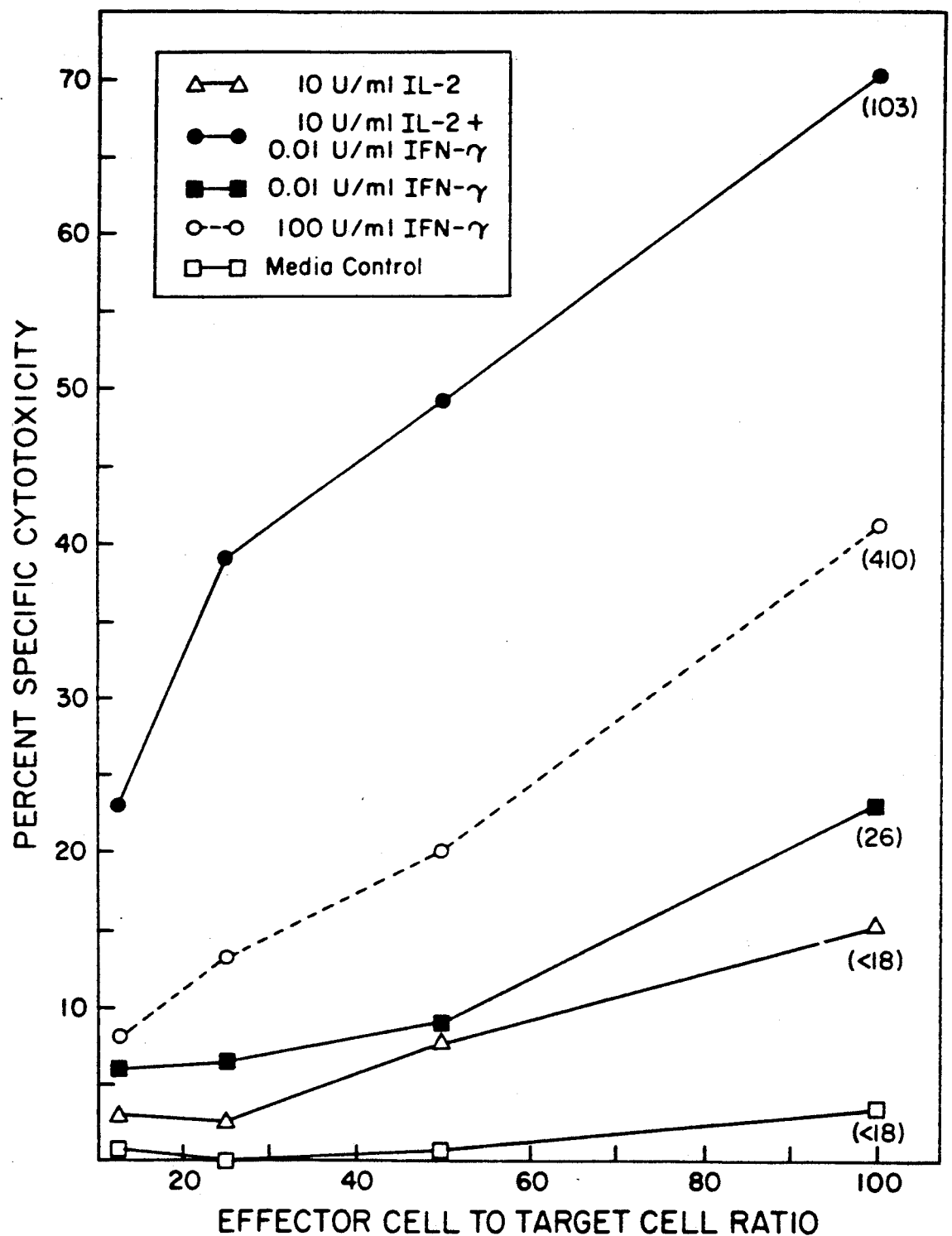

GAMMA INTERFERON-INTERLEUKIN-2 SYNERGISM

This application is a continuation of application Ser. No. 06/904,824 filed Sept. 8, 19 now abandoned, which is a continuation of application Ser. No. 06/571,174, filed Jan. 6, 19 now abandoned.

FIELD

The present invention relates to the field of inhibition of tumor cell growth, specifically using cytotoxic and cytolytic agents. In particular, the present invention relates to the combined use of interleukin-2 (IL-2) and gamma interferon (IFN-γ) in such inhibition. Further background material is incorporated herein by reference by way of parenthetical numerical citation in the text to the appended bibliography.

BACKGROUND

Both IL-2 and IFN-γ have demonstrated an ability to activate natural killer (NK) cell activity (1-6). A theory is that such IL-2 activity results from induction of IFN-γ (7,8). See also (9,10). NK cells, a component of natural cell-mediated cytotoxicity (NCMC), have been defined by their ability to lyse neoplastic cells in vitro without definable prior activation (11). IL-2 can be obtained from natural source or via recombinant DNA technology (12-17). Gamma interferon (IFN-γ) has been prepared via recombinant technology as well (18,19).

Thus, the nature and tumor inhibition activity of both of these compositions is known.

It has previously been shown that IFN-γ exhibits a synergistic effect with α- or β-interferon in assays for cell growth inhibition (20,21), and with lymphotoxin (22).

SUMMARY OF THE INVENTION

This invention concerns the surprising synergism of IL-2 and IFN-γ in cooperating to inhibit the growth of tumor cells. Accordingly, in one aspect the invention is directed to a composition of matter comprising human IFN-γ in admixture with human IL-2 and to a process for the preparation thereof. In other aspects, the invention concerns processes for inhibition of tumor cells using such a mixture, and of treating subject mammals to curb tumor cell growth.

It will be understood that the present invention relates to the concept of synergistic potentiation of biological activity of pharmaceutically pure human IFN-γ and IL-2 combinations in all aspects and is not to be construed as limited to any specific embodiment described explicitly or implicitly herein except as is encompassed by the lawful scope of the appended claims.

BRIEF DESCRIPTION OF THE DRAWING

FIG. 1 shows synergistic augmentation of NCMC.

DETAILED DESCRIPTION

A. Definitions

"Pharmaceutically acceptable" refers to preparations which are in such form as to permit the biological activity of the active ingredients to be unequivocally effective, and which contain no additional components which are toxic to the subjects to which the composition would be administered. Thus, pharmaceutically acceptable compositions or excipients refer to compositions or excipients which can reasonably be administered to a subject mammal to provide an effective dose of the active ingredient employed.

"Compositions" containing human IFN-γ and IL-2 in synergistically effective amounts refers both to compositions prepared by pre-mixing these active ingredients in vitro and to composition which result from tandem administration of each of these two active ingredients either in solution or admixture with excipients to a subject mammal.

"Synergism" in the context of this invention is defined according to the accepted definition (23). This is most easily seen in terms of the construction of an "isobologram" which plots the dosage levels required for a specific identical biological response of each of two ingredients along the X and Y axes. While simply additive effects would generate a straight line as one ingredient diminishes and the other increases, synergistic effects can be recognized by the generation of a concave curve, such that only a small increase in one component compensates for a drastic decrease in the amount of the other.

B. Examples; Preferred Embodiment

IL-2 and IL-2 assay. A complementary DNA sequence encoding the mature IL-2 protein was engineered for expression in *E. coli*. Recombinant human IL-2 was purified to greater than 95 percent as determined by high pressure liquid chromatography and SDS polyacrylamide gel electrophoresis. The specific activity as determined by a T cell growth assay employing IL-2-dependent CTLL-A11 cells (24) was $1 \times 10^7$ U/mg. A stock solution of $1 \times 10^6$ U/ml contained less than 1 ng/ml endotoxin as determined by the Limulus amebocyte lysate assay (25) and lacked detectable IFN-γ activity.

IFN-γ and IFN-γ assay. Homogeneous recombinant human IFN-γ (specific activity = $6 \times 10^7$ U/mg; (18) was employed in these studies. A stock solution of $1 \times 10^7$ U/ml contained less than 0.01 ng/ml endotoxin as determined by the Limulus amebocyte lysate assay. Antiviral activity was determined by inhibition of cytopathic effect in microtiter assays (26) employing encephalomyocarditis virus and A549 cells (human lung carcinoma) obtained from the American Type Culture Collection (ATCC No. CCL185, Rockville, Md.).

NCMC assay. The target cells used were human A549 cells and human K562 erythroleukemia cells (Dr. Chris D. Platsoucas, Sloan-Kettering Institute). These cells were maintained in Eagle's minimal essential medium supplemented with 1 mM sodium pyruvate, 0.1 mM nonessential amino acids, 2 mM L-glutamine, two-fold vitamin solution, 100 U/ml penicillin, 100 ng/ml streptomycin (Grand Island Biological Co., Grand Island, N.Y.) and 10 percent heat-inactivated fetal bovine serum (Sterile Systems, Inc., Logan, Utah; CMEM).

The NCMC assay was performed as previously described (11). Briefly, target cells ($4-6 \times 10^6$ in 0.4 ml of CMEM) were labelled with 510μCi $Na_2[^{51}Cr]O_4$ (5 mCi/ml, Amersham Corp., Arlington Heights, Ill.) for 1 h at 37° C., followed by three washes in CMEM. Human PBMC (American Red Cross—Northeast Region, Needham, Mass.), purified by Ficoll-Paque (Pharmacia Fine Chemicals, Piscataway, N.J.) gradients were used as effector cells. The PBMC ($3 \times 10^6$/ml) were cultured in 5 ml of CMEM in 15 ml plastic centrifuge tubes (Corning Glass Works, Corning, N.Y.) with the activating agents for 18 h (unless otherwise noted) at 37° C. and washed three times with CMEM. One-tenth ml aliquots of $^{51}$Cr-labelled tumor cells ($1\times10^5$/ml) were added to triplicate 0.1 ml aliquots of effector cells (varying from effector to target ratios of 100:1 to 12.5:1) in round-bottomed microtiter plates (Costar, Cambridge, MA). After 4 h incubation at 37° C., the supernatants were harvested (Skatron, Flow Labs., Rockville, Md.) and counted in a gamma counter. The spontaneous release, as determined by incubating labelled targets in CMEM alone, did not exceed 15 percent of the maximum release that was determined by adding 1 percent nonidet P-40 (Sigma, St. Louis, Mo.). The percent specific cytoxicity was calculated as follows:

$$\frac{\text{CPM EXPERIMENTAL }^{51}\text{Cr RELEASE} - \text{CPM SPONTANEOUS }^{51}\text{Cr RELEASE}}{\text{CPM MAXIMUM }^{51}\text{Cr RELEASE} - \text{CPM SPONTANEOUS }^{51}\text{Cr RELEASE}} \times 100$$

The standard deviations, of three replicates, did not exceed 5 percent.

IFN-γ production. Ficoll-Paque purified PBMC were cultured in ml CMEM in 24 well tissue culture plates (Costar, Cambridge, Mass.) at a concentration of $3\times10^6$ PBMC/ml. Phytohemagglutinin (Wellcome Reagents Limited, Beckenham, England) at a final concentration of 2 μg/ml was used. IFN activity was measured after 24 h of culture at 37° C.

Neutralization of IFN-γ activity. Rabbit anti-recombinant human IFN-γ was used. The antiviral neutralization titer was 50,000 U/ml. Neutralization of IFN-γ activity was performed by adding 100 μl of serum just prior to the addition of reagents used to enhance NCMC.

IL-2 induction of IFN-γ production. Human PBMC were cultured with IL-2 for 24 h. Cell-free supernatants were obtained and assayed for IFN activity. Significant levels of IFN activity were observed in all supernatants obtained from treatment with 100 U/ml and 1000 U/ml of recombinant IL-2. No IFN was detected in supernatants of untreated cells. When the PHA was included with the IL-2 treatments, increased levels of IFN were detected in the cell supernatants. Augmentation of IFN production, in combination treatment with 1000 U/ml IL-2 and PHA averaged 5 fold. The IFN produced after IL-2 treatment of PBMC was totally neutralized by anti-recombinant IFN-γ.

IL-2 augmentation of NCMC. Human PBMC were treated with varying doses of purified recombinant human IL-2 (0.5 U/ml to 500 U/ml) for 18 h and tested for NCMC using A549 targets. Significant enhancement of NCMC was observed in a dose dependent manner at all IL-2 treatments greater than 0.5 U/ml. The positive assay control (treatment with 100 U/ml purified recombinant human IFN-γ) demonstrated significant enhancement of NCMC (57 percent) when compared to the media control treatment (25 percent at E:T=100:1). It should be noted that treatment of PBMC with 2500 U/ml of IFN-γ did not increase the level of NCMC when compared to treatment with 100 U/ml IFN-γ. Similar results have been found employing K562 cells as targets. Supernatants obtained after 18 h of PBMC culture demonstrated antiviral titers of 1400 U/ml and 129 U/ml IFN-γ for 500 U/ml IL-2 and 50 U/ml IL-2 treatments, respectively. Treatment with 100 U/ml IFN-γ produced 259 U/ml IFN-γ; other treatments failed to elicit detectable antiviral activity.

IL-2 exposure requirement. Significant enhancement of NCMC using A549 targets resulted after 5 min of treatment with 1000 U/ml IL-2, and after 15 min with 100 U/ml IL-2 or 100 U/ml IFN-γ ($p<0.001$, Student's t test). Significant enhancement of NCMC was also observed after 5 min of exposure to IL-2 when K562 cells are used as targets.

When supernatants (collected after 18 h of PBMC culture) were assayed for antiviral activity, no detectable IFN was found unless IL-2 was present in the PBMC cultures for a period of 3 hours or greater. Thus, significant enhancement of NCMC resulted after IL-2 treatment without detectable IFN production.

Neutralization of NCMC enhancement. Enhancement of NCMC by treatment with recombinant IL-2 was found to be partially neutralized by anti-IFN-γ. For treatment with 100 U/ml IL-2, specific lysis was reduced from 72 percent to 42 percent when anti-IFN-γ was added. Thus, significant NCMC was still present. When treatment of 100 U/ml IFN-γ was used as a control, specific lysis was reduced from 62 percent to 17 percent in the presence of anti-IFN-γ (not significantly different from 16 percent specific lysis obtained by treatment with anti-IFN-γ alone). The antiviral assay confirmed complete neutralization of the IFN-γ activity in anti-IFN-γ treated cultures.

Synergistic augmentation of NCMC. A representative experiment, of six experiments performed, involving combination IL-2 and IFN-γ treatment on NCMC is displayed in FIG. 1. At an effector cell to target cell ratio of 100:1, significant enhancement resulted by treatment with 0.01 U/ml IFN-γ (22 percent) or 10 U/ml IL-2 (13 percent) alone. However, in combination these treatments augmented NCMC enhancement (70 percent) significantly higher than could be achieved by either treatment alone. $3\times10^6$ Ficoll-Paque purified PBMC were cultured with 0.01 U/ml IFN-γ and 10 U/ml of IL-2 at 37° C. After 18 h, the PBMC were washed 3 times in CMEM and used as effectors in an NCMC assay as described on pages 4 and 5.

Supernatants collected at the end of PBMC culture (18 h) were examined for IFN antiviral activity. Supernatants obtained from IL-2 treatment, IFN treatment and the combination treatment contained <18 U/ml, 26 U/ml and 103 U/ml IFN activity, respectively. The positive assay control supernatant (treatment of 100 U/ml IFN-γ) contained 410 U/ml IFN. It should be emphasized that the level of NCMC obtained from the positive control was significantly lower than that of the combination treatment (which supernatant contained significantly lower levels of IFN-γ activity).

Thus, when PBMC were treated simultaneously with IL-2 and IFN-γ a synergistic level of NCMC enhancement occurred. The increased level of NCMC activity was not due to IFN-γ produced by IL-2 treatment. One possible explanation may be that treatment of IFN-γ increases IL-2 receptor-bearing NK cells or increases the activity of the IL-2 receptor for IL-2. Studies with murine NK cells have demonstrated higher levels of NK enhancement after combined treatment with IL-2 and IFN (3, 10).

Both recombinant human IL-2 and IFN-γ were shown to require only a brief period of exposure in order to activate PBMC to enhance NCMC. These findings support the clinical use of these lymphokines despite the possibility that the in vivo half-lives of both natural and recombinant lymphokines may be short (27), suggest that IL-2 alone can enhance NCMC, even when IFN-γ is undetectable and demonstrate IL-2 has a greater range of biological activities than previously suggested.

C. Utility and Administration

Administration of the compositions hereof can be via any of the accepted modes of administration for agents which exhibit such activity. These methods include oral, parenteral or topical administrations and otherwise systemic forms. Local or intravenous injection is preferred.

Depending on the intended mode of administration, the compositions used may be in the form of solid, semi-solid or liquid dosage forms, such as, for example, tablets, pills, capsules, powders, liquids, suspensions, or the like, preferably in unit dosage forms suitable for single administration of precise dosages. The compositions will include a conventional pharmaceutical carrier or excipient and, in addition, may include other medicinal agents, pharmaceuticals agents, carriers, adjuvants, etc. Such excipients may include other proteins, such as, for example, human serum albumin or plasma preparations.

For solid compositions, conventional nontoxic solid carriers include, for example, pharmaceutical grades or mannitol, lactose starch, or magnesium stearate. Liquid pharmaceutically administerable compositions can, for example, be prepared by dissolving, dispersing, etc. in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate or sorbitan monolaurate. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active component(s) in an amount effective to achieve the desired effect in the subject being treated.

The amount of active compound administered will, of course, be dependent on the subject being treated, the severity of the affliction, the manner of administration and the judgment of the prescribing physician.

While extrapolation from in vitro levels to in vivo levels is not completely predictable, it is estimated that a suitable composition for treating a subject mammal with the composition of the invention sufficient to inhibit tumor growth would range from a combination of about $10^2$ units of human IFN-γ with $10^2$ units of human IL-2 per kg of body weight to a combination of about $10^6$ units of IFN-γ with about $10^6$ units of IL-2 per kg of body weight. However, the invention cannot be restricted to these specific ranges because of the variability in severity of affliction, and the susceptibility of the individual patient as noted above.

Bibliography

1. Gillis, S., and Smith, K.A., 1977. Long term culture of tumour-specific cytotoxic T cells. Nature. 268: 154.
2. Nabholz, M., Engers, H., Collavo, D., and North, M., 1978. Cloned T-cell lines with specific cytolytic activity. Curr. Topics Microbiol. Immun. 81: 176.
3. Henney, C.S., Kuribayashi, K., Kern, D.E., and Gillis, S., 1981. Interleukin-2 augments natural killer cell activity. Nature (London). 291: 335.
4. Lattime, E.C., Pecoraro, G.A., and Stutman, O., 1983. The activity of natural cytotoxic cells is augmented by interleukin 2 and interleukin 3. J. Exp. Med. 157: 1070.
5. Teh, H.-S., and Yu, M., 1983. Activation of nonspecific killer cells by interleukin 2-containing supernatants. J. Immunol. 131: 1827.
6. Handa, K., Suzuki, R., Matsui, H., Shimizu, Y., and Kumagai, K., 1983. Natural killer (NK) cells as a responder to interleukin 2 (IL 2). II. IL 2-induced interferon γ production. J. Immunol. 130: 988.
7. Weigent, D.A., Stanton, G.J., and Johnson, H.J., 1983. Interleukin 2 enhances natural killer cell activity through induction of gamma interferon. Infect. Immun. 41: 992.
8. Kawase, 1., Brooks, C.G., Kuribayashi, K., Olabuenaga, S., Newman, W., Gillis, S. and Henney, C.S., 1983. Interleukin 2 induces-interferon production: Participation of macrophages and NK-like cells. J. Immunol. 131: 288.
9. Minato, N., Reid, L., and Bloom, B.R., 1981. On the heterogeneity of murine natural killer cells. J. Exp. Med. 154: 750.
10. Kuribayashi, K., Gillis, S., Kern, D.E., and Henney, C.S., 1981. Murine NK cell cultures: effects of interleukin 2 and IFN on cell growth and cytotoxic activity. J. Immunol. 126:2321.
11. Herberman, R.B., and Holden, H.T., 1978. Natural cell-mediated immunity. Adv. Cancer Res. 27: 305.
12. Parker et al., J. Immunol. 127, 1983 (1981).
13. Stadler et al., J. Immunol. 128, 1620 (1982).
14. U.S. Pat. No. 4401756 and therein cited references.
15. European Patent Application Publn. No. 0064401.
16. European Patent Application Publn. No. 0088195.
17. European Patent Application Publn. No. 0089062.
18. Gray, P.W., Leung, D.W., Pennica, D., Yelverton, E., Najarian, R., Simonsen, C.C., Derynck, R., Sherwood, P.J., Wallace, D.H., Berger, S.L., Levinson, A.D., and Goeddel, D.V., 1982. Expression of human immune interferon cDNA in *E. coli* and monkey cells. Nature. 295: 503.
19. European Patent Application Publn. No. 0077670.
20. U.S.S.N. 436758, filed 25 October 1982.
21. Czarniecki et al., J. Virology 49, (1984).
22. U.S.S.N. 499952, filed 1 June 1983.
23. Goodman, et al., *The Pharmacological Basis of Therapeutics*, MacMillan Publishing Co. Inc., New York (1980).
24. Palladino, M.A., Ranges, G.E., Scheid, M.P., and Oettgen, H.F., 1983. Suppression of T cell cytotoxicity by nude mouse spleen cells: Reversal by monsaccharides and interleukin 2. J. Immunol. 130: 2200.
25. Levin, J., Tomasulo, P.A., and Oser, R.S., 1970. Detection of endotoxin in human blood and demonstration of an inhibitor. J. Lab. Clin. Med. 75: 903.
26. Svedersky, L.P., Hui, A., Don, G., Wheeler, D., McKay, P., May, L., and Stebbing, N., 1982. Induction and augmentation of mitogen-induced lymphokine production in human PBL by N-desacetyl-thymosin-1. In: Human Lymphokines, A. Khan and N.O. Hill, eds. Academic Press, New York. 125.
27. Donohue, J.H. and Rosenberg, S.A., 1983. The fate of interleukin-2 after *in vivo* administration. J. Immunol. 130:2203.

I claim:

1. A process for inhibiting tumor cell growth which comprises administering to a subject mammal in need of such treatment synergistically effective amounts of human IL-2 and human IFN-$\gamma$.

2. A composition for inhibiting tumor cell growth, consisting essentially of human IFN-gamma made in recombinant cell culture and human IL-2 made in recombinant cell culture, said IFN-gamma and IL-2 being present in synergistically effective amounts.

3. The process of claim 11 wherein the synergistically effective amounts are about $10^2$ units of human IFN-$\gamma$ and about $10^2$ units of human IL-2 per Kg of body weight to about $10^6$ units of human IFN-$\gamma$ and about $10^6$ units of IL-2 per Kg of body weight.

4. A process for inhibiting tumor cell growth which comprises administering to a tumor cell an effective amount of a composition comprising synergistically effective amounts of recombinant human IFN-gamma and recombinant human IL-2.

* * * * *

UNITED STATES PATENT AND TRADEMARK OFFICE
CERTIFICATE OF CORRECTION

PATENT NO. : 5,082,658
DATED : January 21, 1992
INVENTOR(S) : MICHAEL A. PALLADINO It is certified that error appears in the above-identified patent and that said Letters Patent is hereby corrected as shown below:

Col. 1, delete lines 5-8, and insert the following:

--This application is a continuation of Ser. No. 06/904,824, filed September 8, 1986, now abandoned, which is a continuation of Ser. No. 06/571,174, filed January 16, 1984, now abandoned.--

Col. 2, line 60, change "510µCi" to --150µCi--.

IN THE CLAIMS

Col. 8, line 1, change "claim 11" to --claim 1--.

Signed and Sealed this

Thirteenth Day of July, 1993

Attest:

MICHAEL K. KIRK

*Attesting Officer*    Acting Commissioner of Patents and Trademarks